United States Patent
Dias et al.

(10) Patent No.: US 9,951,183 B2
(45) Date of Patent: Apr. 24, 2018

(54) AMPHIPHILIC BLOCKCOPOLYMERS COMPRISING REDUCTION SENSITIVE BIODEGRADABLE POLYESTERAMIDES

(71) Applicant: DSM IP Assets B.V., Heerlen (NL)

(72) Inventors: Aylvin Jorge Angelo Athanasius Dias, Echt (NL); Zhiyuan Zhong, Echt (NL); Huanli Sun, Echt (NL); Wei Wang, Echt (NL); Fenghua Meng, Echt (NL); Jan Feijen, Echt (NL)

(73) Assignee: DSM IP ASSETS, B.V., Heerlen (NL)

( * ) Notice: Subject to any disclaimer, the term of this patent is extended or adjusted under 35 U.S.C. 154(b) by 0 days.

(21) Appl. No.: 15/502,228

(22) PCT Filed: Aug. 10, 2015

(86) PCT No.: PCT/EP2015/068371
§ 371 (c)(1),
(2) Date: Feb. 7, 2017

(87) PCT Pub. No.: WO2016/020547
PCT Pub. Date: Feb. 11, 2016

(65) Prior Publication Data
US 2017/0218123 A1 Aug. 3, 2017

(30) Foreign Application Priority Data

Aug. 8, 2014 (CN) .......................... 2014 1 0387651
Sep. 17, 2014 (EP) ..................................... 14185197

(51) Int. Cl.
C08G 63/02 (2006.01)
C08G 69/44 (2006.01)

(52) U.S. Cl.
CPC .................................... *C08G 69/44* (2013.01)

(58) Field of Classification Search
None
See application file for complete search history.

(56) References Cited

U.S. PATENT DOCUMENTS

| | | |
|---|---|---|
| 2003/0144373 A1 | 7/2003 | Bowman et al. |
| 2003/0236371 A1 | 12/2003 | Wilson et al. |
| 2005/0065314 A1 | 3/2005 | Lai |
| 2007/0155926 A1 | 7/2007 | Matyjaszewski et al. |

FOREIGN PATENT DOCUMENTS

| | | |
|---|---|---|
| WO | 2008048298 | 4/2008 |
| WO | 2009088912 | 7/2009 |

OTHER PUBLICATIONS

Meng, F., et al., "Reduction-sensitive polymers and bioconjugates for biomedical applications", Biomaterials, Elsevier Science Publishers BV., Barking, GB., vol. 30, No. 12, Apr. 1, 2009 (Apr. 1, 2009). Journal, Society of Polymer Science, (1994), pp. 49-59. , . . . Kobayashi, et al.,"Kinetics of the Addition Reactions of Thiobenzoic Acids to Styrenes or Ethynlybenzenes as the Model of Polyaddition. Study on the Rate-Determining Step and Substituent Effect." Polmyer Journal, Society of Polymer Science, (1993) pp. 507-520,.
Kobayashi, et al., "Synthesis of New Linear Polymers containing Thiocarbonyl Groups: Polyaddition of Dicarbothioic Acid to Diolefins," Polymer Journal, Society of Polymer Science, (1994), pp. 49-59.
Kobayashi, et al.,"Kinetics of the Addition Reactions of Thiobenzoic Acids to Styrenes or Ethynlybenzenes as the Model of Polyaddition. Study on the Rate-Determining Step and Substituent Effect." Polmyer Journal, Society of Polymer Science, (1993) pp. 507-520.
Marvel, et al., "Polythiolesters", Journal of the American Chemical Society, (1951), pp. 1100-1102.
WO2016020547 International Search Report, dated Sep. 2, 2015.
WO2007/028612 International Search Report, dated Mar. 11, 2008.

*Primary Examiner* — Terressa Boykin
(74) *Attorney, Agent, or Firm* — Kevin M. Bull (57) ABSTRACT

The present invention relates to amphiphilic block copolymers comprising reduction sensitive biodegradable polyesteramides. The present invention also relates to micelles comprising the amphiphilic block copolymers. The invention also relates to drug delivery systems comprising the micelles. The amphiphilic block copolymers comprise hydrophilic and hydrophobic blocks whereby the hydrophobic blocks comprise a biodegradable polyesteramide based on alpha-amino acids, diols, aliphatic dicarboxylic acids and optionally diamines whereby at least one of the dicarboxylic acids, diols or diamines comprises disulphide linkages.

20 Claims, 5 Drawing Sheets

AMPHIPHILIC BLOCKCOPOLYMERS COMPRISING REDUCTION SENSITIVE BIODEGRADABLE POLYESTERAMIDES

This application is a US National Phase application of International Application No. PCT/EP2015/068371, filed 10 Aug. 2015, which designated the US and claims priority to Chinese Application No. 201410387651.0, filed 8 Aug. 2014, and European application number 14185197.2, filed 17 Sep. 2014, the entire contents of each of which are hereby incorporated by reference.

The present invention relates to amphiphilic block copolymers comprising reduction sensitive biodegradable polyesteramides. The present invention also relates to micelles comprising the amphiphilic block copolymers. The invention also relates to drug delivery systems comprising the micelles.

The field of the present invention is the area of formulating hydrophobic drugs for use in aqueous systems, in particular, the formulation of relatively insoluble and/or toxic hydrophobic drugs such as anticancer agents. Currently, potentially hydrophobic drugs have properties that can result in their classification as "challenging" (poorly-water-soluble) compounds. Such molecules have favorable in vitro capabilities, however due to characteristics such as poor aqueous solubility, toxicity, chemical instability and limited cellular permeability, these compounds require formulation to be effective (Davis, S. S. et al. (1998) Int. J. Pharm. 179, 2).

Amphiphilic block copolymers have been used to formulate such challenging compounds (Jones, M. C et al. (1999) Eur. J. Pharm. Biopharm. 48, 101). The amphiphilic block copolymers comprised of hydrophobic and hydrophilic blocks, can assemble into a microphase separated, core/shell architecture in a selective solvent, this architecture is further called a micelle. In an aqueous environment, the hydrophobic compound will be encapsulated into the hydrophobic core of the micelle while the aqueous solubility is provided by the shell of the micelle. Due to their nanoscopic dimensions and properties imparted by the shell, micelles may have long-term circulation capabilities.

Recently there has been growing interest in biodegradable polymers for intracellular and triggered delivery of small molecule drugs and biologics (DNA, RNA and therapeutic peptides and proteins).

The use of biodegradable polymers for intracellular drug delivery is known in the art. In Biomaterials 30 (2009) 2180-2198, F. Meng, W. E. Hennink, Z. Zhong reduction sensitive polymers are disclosed which comprise disulphide bonds as the reductive group. These reduction sensitive polymers can be incorporated in the main or side chain of the polymer for the delivery of bioactive agents. These polymers are reported in the form of micelles, polymersomes, micro- and nanogels but also as multi-layered thin films or nanotubes.

For intracellular delivery typically a more reductive environment is required since the cell cytoplasm is a more reductive environment than the extracellular environment.

A disadvantage is however that most biodegradable polymers are hydrolytically degradable which makes them unstable in extracellular fluids. There is thus a high risk of premature degradation and clearance of the polymer and drug reaching the target site for triggered release. This in turn means that higher dosages of drugs are required and these higher doses and their release in sites other than the targeted site can cause side effects.

There is a long felt need in the art for amphiphilic block copolymers for encapsulating poorly (water) soluble drugs such as anti-cancer agents. Desirably the encapsulated drugs are nanoscopic in size, thermodynamically and kinetically stable, can protect the poorly (water) soluble or hydrophobic drugs from self-aggregation and provide advantageous release rates.

The object of the present invention is to provide amphiphilic block copolymers which can be processed into micelles which are thermodynamically and kinetically stable and which protect hydrophobic drugs from self-aggregation and provide advantageous release properties for intracellular delivery.

The object of the invention is also to develop triggered intracellular delivery systems for anti-cancer agents such as doxorubicin (DOX) which may lead to enhanced cancer chemotherapy.

The object of the present invention is achieved by providing amphiphilic block copolymers comprising hydrophilic and hydrophobic blocks whereby the hydrophobic blocks comprise a biodegradable polyesteramide comprising disulphide linkages in the backbone of the polyesteramide.

Polyesteramides comprising disulphide linkages is further referred to as PEA-SS.

More preferably the biodegradable polyesteramides comprise alpha-amino acids, diols, aliphatic dicarboxylic acids and optionally diamines whereby at least one of the dicarboxylic acids, diols or diamines comprises disulphide linkages.

Most preferably the hydrophobic blocks comprise at least a biodegradable polyesteramide of one of the following structural formulas I, II or III Formula I Formula II Formula III Wherein m varies from 5 to 300 and whereby

Y is independently selected from the group consisting of aliphatic or cycloaliphatic hydrocarbons. selected from the group consisting of $(C_2-C_{20})$ aliphatic or cycloaliphatic hydrocarbons.

X is independently selected from the group consisting of aliphatic, cycloaliphatic or aromatic hydrocarbons.

R is independently selected from the group consisting of a side chain residue of alpha-amino acids with positively charged groups, a side chain residue of amino acids with negatively charged groups, a side chain residue of amino acids with uncharged side groups or a side chain residue of amino acids with hydrophobic groups.

More preferably R is independently selected from the group consisting of a side chain residue of amino acids with positively charged groups chosen from arginine, histidine or lysine, a side chain residue of amino acids with negatively charged groups chosen from aspartic acid or glutamic acid, a side chain residue of amino acids with uncharged side groups chosen from serine, threonine, asparagine, glutamines, cysteine, seleno cysteine, glycine and proline or a side chain residue of aminoacids with hydrophobic groups chosen from alanine, valine, isoleucine, leucine, methionine, tyrosine, tryptophan or phenylalanine.

The polyesteramides of formula I, II or III comprise Y which is independently selected from the group consisting of aliphatic or cycloaliphatic hydrocarbons. The aliphatic or cycloaliphatic hydrocarbon is preferably selected from a $(C_2-C_{20})$ aliphatic or cycloaliphatic hydrocarbon. More preferably Y is selected from $(C_2-C_{20})$alkylene, $(C_2-C_{20})$alkenylene, bicyclic-fragments of 1,4:3,6-dianhydrohexitols of structural formula (IV) and combinations thereof.

Formula (IV)

The polyesteramides comprise X which is independently selected from the group consisting of aliphatic, cycloaliphatic or aromatic hydrocarbons. The aliphatic hydrocarbon is preferably selected from a $(C_2-C_8)$ hydrocarbon such as $-(CH_2)_2-$, $-(CH_2)_3-$, $-(CH_2)_4-$, $-(CH_2)_5-$, $-(CH_2)_6-$, $-(CH_2)_7-$, $-(CH_2)_8-$.

More preferably the amphiphilic block copolymers according to the present invention comprise a biodegradable polyesteramide of structural formula I in which R is selected from a side chain residue of the alpha amino acids chosen from arginine or phenylalanine.

The molecular mass of the polyesteramide is preferably from 500~20,000 g/mol. More preferably from 1,000~10,000 g/mol. The molar mass can be measured via Gel permeation chromatography as disclosed in WO9710849.

The in vitro and in vivo degradation of the biodegradable polyesteramide blocks is well understood and the degradation products are naturally occurring compounds that are readily metabolized and/or eliminated by the patient's body.

The term "biodegradable" refers to material which is capable of being completely or substantially degraded or eroded when exposed to an in vivo environment or a representative in vitro. A polymer is capable of being degraded or eroded when it can be gradually broken-down, resorbed, absorbed and/or eliminated by, for example, hydrolysis, enzymolysis, oxidation, metabolic processes, bulk or surface erosion, and the like within a subject.

The term "disulphide linkages" refers to a disulfide bond which is a covalent bond. The linkage is also called an SS-bond or disulfide bridge, (R—S—S—R). The "disulphide linkages" are present in the backbone of the PEA.

The term "backbone" refers to the main chain of a polymer comprising series of covalently bounded atoms that together create the continuous chain of the polymer.

The synthesis of PEA-SS may comprise the following three basic steps:
(i) Synthesis of disulfide containing di-p-toluenesulfonic acid salts of bis-L-phenylalanine ester (Phe(SS)-2TsOH);
(ii) Synthesis of di-p-nitrophenyl esters of adipic acid (Di-NP-adipate);
(iii) Solution polycondensation of monomers Phe(SS)-2TsOH and Di-NP-adipate at different molar The amphiphilic blockcopolymers according to the present invention also comprise hydrophilic blocks such as for example polyoxazoline, polyvinylpyrollidone or polyalkylene glycol such as polyethylene glycol (PEG). PEG is preferably chosen because of its unique biocompatibility, nontoxicity, hydrophilicity and solubilization properties. It is however also possible to use PEG copolymers comprising L-amino acids. Examples include, without limitation, poly(ethylene glycol)-b-poly(beta-benzyl-L-glutamate), poly(ethylene glycol)-b-poly(L-lysine), poly(ethylene glycol)-b-poly(aspartic acid), poly(ethylene glycol)-b-poly(beta-benzyl-L-aspartate), and acyl esters of the foregoing block copolymers.

The molecular mass of the hydrophilic blocks is preferably from 200~20,000 g/mol and more preferably from 1,000~15,000 g/mol. The content of the hydrophilic blocks is from 20~70 wt. % percent, preferably 30~60 wt. % percent based on the total weight of the amphiphilic block copolymer.

The amphiphilic block copolymers of the present invention are for example AB di-blocks in which A is hydrophilic and B is hydrophobic or ABA- or BAB-tri-block copolymers. Both ABA and BAB type triblock copolymers may be synthesized by ring opening polymerization, or condensation polymerization according to reaction schemes disclosed in U.S. Pat. No. 5,683,723 and U.S. Pat. No. 5,702,717.

In a preferred embodiment the amphiphilic block copolymers are triblock copolymers comprising poly(ethylene oxide) as the hydrophilic block and a polyesteramide of Formula I as the hydrophobic block whereby R is selected from a side chain residue of arginine or phenylalanine.

The molar mass of the amphiphilic block copolymers and the molar mass of the hydrophobic and hydrophilic blocks can be measured via Gel permeation chromatography as disclosed in WO9710849.

The present invention further relates to micelles/nanoparticles comprising the amphiphilic block copolymers according to the invention. The micelles of the present invention exhibit good properties on controlled release, shelf-life and exhibiting long circulation times in vivo. The micelles of the present invention are capable of controlling the release of bioactive agents, especially hydrophobic drugs such as anti-cancer agents in an intracellular environment. Such micelle compositions can offer several advantages over conventional dosage forms such as, decreased systemic side effects, extended effective residence time of the drug, enhanced efficacy (passive targeting to the tumor site), maintenance of therapeutic levels of the drug for longer time and with narrower fluctuations of drug's concentration in the plasma.

The hydrophobic drugs as used herein are compounds which are not freely soluble in water and which are encapsulated within the amphiphilic block copolymers of the present invention. Examples of the hydrophobic drugs include anticancer agents, anti-inflammatory agents, antifungal agents, antiemetic's, antihypertensive agents, sex hormones, and steroids. Typical examples of the hydrophobic drugs are: anticancer agents such as paclitaxel, camptothecin, doxorubicin (DOX), daunomycin, cisplatin, 5-fluorouracil, mitomycin, methotrexate and etoposide; antiinflammatory agents such as indomethacin, ibuprofen, ketoprofen, flubiprofen, diclofenac, piroxicam, tenoxicam, naproxen, aspirin, and acetaminophen; antifungal agents such as itraconazole, ketoconazole, and amphotericin; sex hormons such as testosterone, estrogen, progesterone, and estradiol; steroids such as dexamethasone, prednisolone, and triamcinolone; antihypertensive agents such as captopril, ramipril, terazosin, minoxidil, and parazosin; antiemetic's such as ondansetron and granisetron; antibiotics such as penicillin's for example B-lactams, chloramphenicol, metronidazole and fusidic acid; cyclosporine and biphenyl dimethyl dicarboxylic acid. Other examples of hydrophobic compounds are vitamins, nutrients, drugs, pharmaceuticals, proteins and peptides, vaccines, genetic materials, (such as polynucleotides, oligonucleotides, plasmids, DNA and RNA), diagnostic agents, and imaging agents.

The hydrophobic drug may be capable of stimulating or suppressing a biological response. The hydrophobic drug may for example be chosen from growth factors (VEGF, FGF, MCP-1, PlGF, anti-inflammatory compounds, anti-thrombogenic compounds, anti-claudication drugs, anti-arrhythmic drugs, anti-atherosclerotic drugs, antihistamines, cancer drugs, vascular drugs, ophthalmic drugs, amino acids, vitamins, hormones, neurotransmitters, neurohormones, enzymes, signalling molecules and psychoactive medicaments.

More examples of hydrophobic drugs are neurological drugs (amphetamine, methylphenidate), alpha1 adrenoceptor antagonist (prazosin, terazosin, doxazosin, ketenserin, urapidil), alpha2 blockers (arginine, nitroglycerin), hypotensive (clonidine, methyldopa, moxonidine, hydralazine minoxidil), bradykinin, angiotensin receptor blockers (benazepril, captopril, cilazepril, enalapril, fosinopril, lisinopril, perindopril, quinapril, ramipril, trandolapril, zofenopril), angiotensin-1 blockers (candesartan, eprosartan, irbesartan, losartan, telmisartan, valsartan), endopeptidase (omapatrilate), beta2 agonists (acebutolol, atenolol, bisoprolol, celiprolol, esmodol, metoprolol, nebivolol, betaxolol), beta2 blockers (carvedilol, labetalol, oxprenolol, pindolol, propanolol) diuretic actives (chlortalidon, chlorothiazide, epitizide, hydrochlorthiazide, indapamide, amiloride, triamterene), calcium channel blockers (amlodipin, barnidipin, diltiazem, felodipin, isradipin, lacidipin, lercanidipin, nicardipin, nifedipin, nimodipin, nitrendipin, verapamil), anti arthymic active (amiodarone, solatol, diclofenac, enalapril, flecainide) or ciprofloxacin, latanoprost, flucloxacillin, rapamycin and analogues and limus derivatives, paclitaxel, taxol, cyclosporine, heparin, corticosteroids (triamcinolone acetonide, dexamethasone, fluocinolone acetonide), anti-angiogenic (iRNA, VEGF antagonists: bevacizumab, ranibizumab, pegaptanib), growth factor, zinc finger transcription factor, triclosan, insulin, salbutamol, oestrogen, norcantharidin, microlidil analogues, prostaglandins, statins, chondroitinase, diketopiperazines, macrocycli compounds, neuregulins, osteopontin, alkaloids, immuno suppressants, antibodies, avidin, biotin, clonazepam.

One of the preferred hydrophobic drugs is doxorubicin (DOX). DOX is one of the most potent anticancer drugs used widely in the treatment of different types of solid malignant tumors. DOX is known to interact with DNA by intercalation and inhibition of macromolecular biosynthesis. It is crucial, therefore, to deliver and release DOX in the cytoplasm and/or right into the cell nucleus.

In the context of the present invention the term "micelle(s)" refers only to the amphiphilic block copolymers assembled into a microphase separated, core/shell architecture in a selective organic solvent. A micelle (plural micelles, micella, or micellae) is an aggregate of amphiphilic molecules dispersed in a liquid. A typical micelle in aqueous solution forms an aggregate with the hydrophilic "head" regions in contact with surrounding solvent, sequestering the hydrophobic regions in the micelle centre. Micelles are approximately spherical in shape. Other phases, including shapes such as ellipsoids, cylinders, and rods are also possible. The shape and size of a micelle is a function of the molecular geometry of its molecules and solution conditions such as concentration, temperature, pH, and ionic strength.

The micelles according to the present invention may comprise a further hydrophobic core excipient such as a fatty acid, a vitamine or any hydrophobic polymer such as for example polycaprolactone. In this way the release properties can be further steered. Also the size of the micelles can be adjusted in this way.

The micelles of the present invention may optionally comprise a lyoprotectant. A lyoprotectant acts as a stabilizer for the loaded micelles during for example freeze drying. In this way the micelles do not coalesce so that the dried product does not readily disperse when an aqueous dispersant is added. The lyoprotectant can be a saccharide or polyol, for example, trehalose, sucrose or raffinose, or another hydrophilic polyol such as maltodextrin, fructose, glycerol, sorbitol, inositol and mannose. Lyoprotectants can also be materials other than sugars such as PEG.

Typically, the ratio of amphiphilic block copolymer to hydrophobic core excipient or lyoprotectant ranges from 1:1 w/w to about 1:50 w/w, preferably from 1:1 w/w to 1:10 w/w, advantageously to 1:5 w/w.

The micelles according to the present invention comprise an average particle size in the range of 5-800 nm, preferably 8-600 nm, more preferably 10-400 nm, most preferably in the range of 25-200 nm. The desired size is strongly dependent on the application and can be adjusted accordingly.

In general, micelles can be fabricated using a variety of techniques such as spray drying, freeze spray evaporation or emulsification (co-solvent evaporation). It is known to the person skilled in the art that the physical and chemical properties of micelles fabricated via emulsification, are greatly depended on the emulsification processing steps one applies for preparing the micelles. For example WO-A-03082303 discloses a process for the preparation of micelles which micelles comprise amphiphilic block copolymers and a hydrophobic drug, and optionally a lyoprotectant. The process steps for producing the micelles include dissolving the hydrophobic drug and the amphiphilic block copolymer in a volatile organic solvent and then adding water to the miscible solution, with mixing, to promote the formation of micelles and the partitioning of the hydrophobic drug into the micelle cores. The water is added slowly to induce micellization through the critical water content of the amphiphilic block copolymers (level of water required for assembly of the amphiphilic block copolymers). The water content is greater than the critical weight concentration (CWC). Subsequently, the organic solvent is removed by evaporation under reduced pressure or elevated temperature. After loading, the micelles based on the amphiphilic block copolymers can be freeze dried for later reconstitution.

Alternatively the micelles can be prepared via the following steps:
a) dissolving the hydrophobic drug and the amphiphilic block copolymer in an organic solvent to form a solution,
b) adding said organic solution into an aqueous medium,
c) optionally repeating aforementioned steps.

The concentration of the amphiphilic block copolymer in the organic solvent depends on the organic solvent used. For example in case that acetone is used as a solvent the concentration of the amphiphilic block copolymer at most 130 mg/L (milligram per liter), preferably is at most 100 mg/L, more preferably is at most 65 mg/L.

The organic solvent is for example a water miscible solvent used to produce a solution with at least one amphiphilic block copolymer and at least one hydrophobic drug. For use in the present methods, the solvent preferably has a boiling temperature lower than that of water (less than 100 degrees centigrade at 1 atm). Preferably, the organic solvent forms an azeotrope with water, advantageously a negative azeotrope. Where the solvent and water form an azeotrope, the azeoptropic mixture can be dried by removing the azeotrope under conditions of decreased pressure and/or elevated temperature. Examples of organic solvents include without limitation, acetone, acetonitrile, methanol, ethanol, acetonitrile, tetrahydrofuran, propanol or isopropanol.

In a preferred embodiment, the organic solvent is selected from the group consisting of acetone, methanol, ethanol, acetonitrile, tetrahydrofuran or mixtures thereof.

The aqueous medium is selected from the group consisting of water, saline solution or a buffer solution with a pH in the range of 1-14.

It is also possible to functionalize at least the surface of the micelles by providing at least the surface with a functional group, in particular with a signaling molecule, an enzyme or a receptor molecule, such as an antibody. The receptor molecule may for instance be a receptor molecule for a component of interest, which is to be purified or detected, e.g. as part of a diagnostic test, making use of the particles of the present invention. Suitable functionalization methods may be based on a method known in the art.

The micelles can be administered, for example oral, via inhalation, parenteral, buccal, sublingual, nasal, rectal, patch, pump or transdermal administration and in pharmaceutical compositions formulated accordingly. Parenteral administration includes intravenous, infraperitoneal, subcutaneous, intramuscular, transepithelial, nasal, intrapulmonary, intrathecal, rectal and topical modes of administration. Parenteral administration may be by continuous infusion over a selected period of time. The micelles can also be administered with an inert diluent or with an edible carrier. The micelles may be enclosed in hard or soft shell gelatin capsule, it may be compressed into tablets or it may be incorporated directly with the food of the diet. For oral therapeutic administration, the micelles may be incorporated within an excipient and used in the form of ingestible tablets, buccal tablets, troches, capsules, elixirs, suspensions, syrups, wafers, and the like. The micelles can also be administered parenterally. Solutions of the micelles can be prepared in water. Under ordinary conditions of storage and use, these preparations contain a preservative to prevent the growth of microorganisms. A person skilled in the art would know how to prepare suitable micelle formulations.

The medical fields wherein the micelles can be used include dermatology, vascular, orthopedics, ophthalmic, spinal, intestinal, pulmonary, nasal, or auricular.

The present invention further relates to drug delivery systems comprising the micelles.

Examples of drug delivery systems include, but are not limited to catheters, stents, rods, implants, coatings, fibers, mats or pads.

In another preferred embodiment, the invention provides for micelles for use as a medicament.

In yet another preferred embodiment, the invention provides for the use of the micelles for the manufacture of a medicament for intracellular delivery.

The present invention will now be described in detail with reference to the following non limiting examples which are by way of illustration only.

EXAMPLES

Example 1

Synthesis of PEG-NH2 from PEG-NPC (Nitro-phenyl-carbonate) Followed by End Modification with Ethylenediamine Part 1. Synthesis of PEG-NPC Synthesis of PEG NPC is a described in Sun H L, Guo B N, Cheng R, et al. Biomaterials 2009; 30(31):6358-66. PEG-NPC is an amino ($-NH_2$) reactive PEG derivative. In brief, under a nitrogen atmosphere, to a DCM solution (70 mL) of mPEG (10.0 g, 2 mmol) and pyridine (0.791 g, 10 mmol), a solution of p-Nitrophenylcarbonate (p-NPC) (1.614 g, 8 mmol) in 15 mL DCM was added dropwise at 0° C. After completion of addition, the reaction mixture was warmed to r.t. and the reaction proceeded for another 20 h. The resulting polymer PEG-NPC was isolated by precipitation in cold diethylether and dried in vacuum. Yield: 94.9%. $^1$H NMR showed NPC functionality close to 100%.

Part 2 Synthesis of PEG-NH$_2$

Under a nitrogen atmosphere, to a DCM solution (10 mL) of ethylenediamine (0.465 g, 7.74 mmol), a solution of PEG-NPC (2.000 g, 0.387 mmol) in DCM (10 mL) was added dropwise at r.t. The reaction was allowed to continue for 24 h. The resulting PEG-NH$_2$ was isolated by precipitation in cold diethylether twice and dried in vacuum. Yield: 78%. 1H NMR (400 MHz, CDCl3), δ (ppm): 5.32 ($-$NH$-$C(O)$-$); 4.22 ($-$CH2-O$-$C(O)$-$NH2); 3.64 (PEG); 3.38 (CH3O$-$); 3.24 ($-$CH2-NH$-$C(O)$-$O$-$); 2.82 ($-$CH2-NH2); 2.75 (NH2-CH2-).

Example 2

Synthesis of PEG-PEA(SS)-PEG Triblock Copolymer.

Amphiphilic triblock copolymer PEG-PEA (SS)-PEG were synthesized via coupling reaction between mPEG-NH$_2$ of example 1 and NP-PEA (SS)-NP (Scheme 1). In brief, under a nitrogen atmosphere, to a DMF solution (0.7 mL) of mPEG-NH$_2$ (0.183 g, 0.036 mmol), a solution of NP-PEA (SS)-NP (0.04 g, 0.0036 mmol) in 0.8 mL DMF was added dropwise at r.t. The reaction is allowed to continue for 3 d at 40° C. The resulting PEG-PEA(SS)-PEG copolymer was isolated by precipitation in cold ethyl acetate, filtrated and washed using ultra-pure water twice and freeze-dried for 2 d.

Example 3

Micelle Formation and Critical Micelle Concentration (CMC).

Micelles of PEG-PEA(SS)-PEG were prepared under stirring by dropwise addition of 0.8 mL PB (10 mM, pH 7.4) to 0.2 mL of block copolymer solution (2 mg/mL) in DMF at r.t. followed by extensive dialysis against PB for 24 hr.

The critical micelle concentration (CMC) was determined using pyrene as a fluorescence probe. The concentration of block copolymer was varied from $3.0 \times 10^{-4}$ to 0.15 mg/mL and the concentration of pyrene was fixed at 0.6 μM. The fluorescence spectra were recorded using FLS920 fluorescence spectrometer with the excitation wavelength of 330 nm. The emission fluorescence at 372 and 383 nm was monitored. The CMC was estimated as the cross-point when extrapolating the intensity ratio $I_{372}/I_{383}$ at low and high concentration regions.

Figure 1:
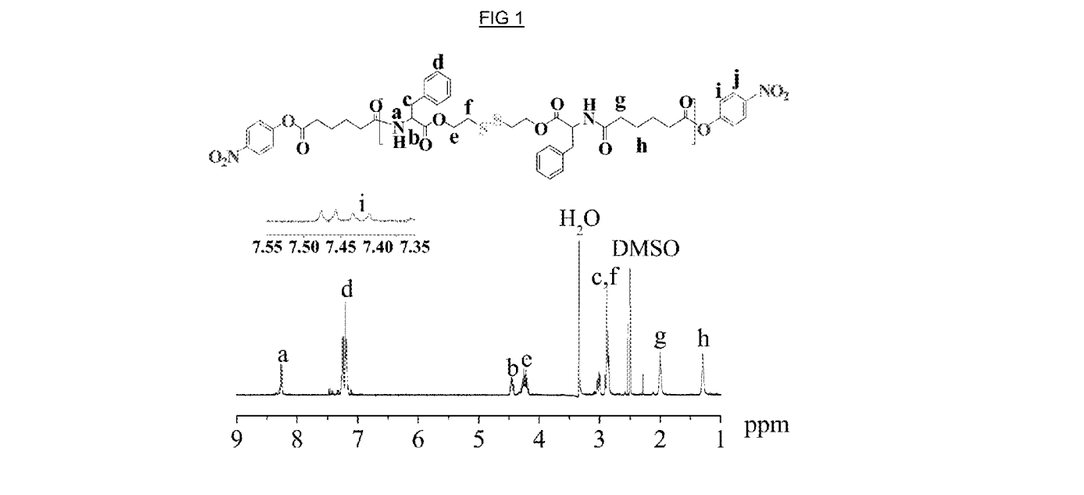
FIG. 1: $^1$H NMR spectrum (400 MHz, DMSO-$d_6$) of NP-PEA(SS)-NP.
Figure 2:
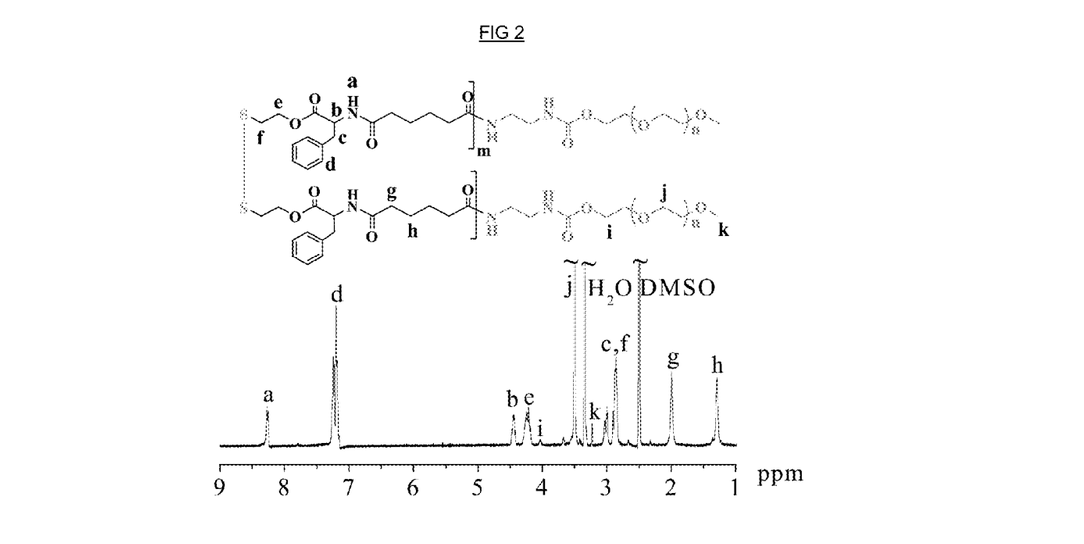
FIG. 2: $^1$H NMR spectrum (400 MHz, DMSO-$d_6$) of PEG-PEA(SS)-PEG triblock copolymer.
Figure 3:
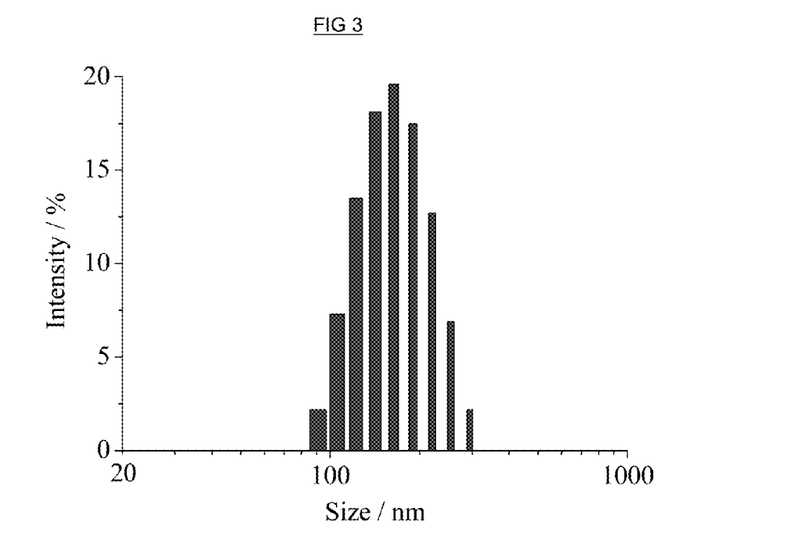
FIG. 3: Size distribution of PEG-PEA(SS)-PEG micelles in PB (10 mM, pH 7.4) determined by DLS
Figure 4:
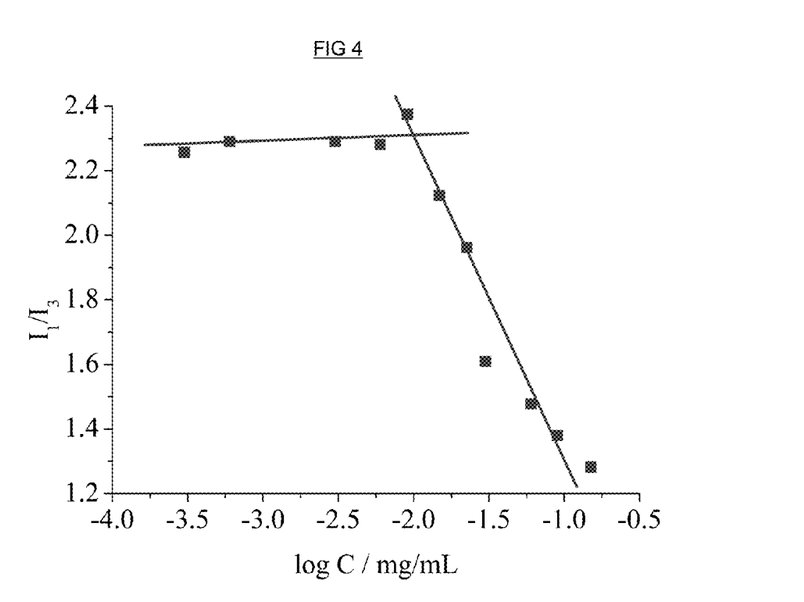
FIG. 4: The fluorescence intensity ratio $I_1/I_3$ of pyrene as a function of PEG-PEA(SS)-PEG concentration. The critical micelle concentration (CMC) in aqueous medium is determined to be ca. $9.9 \times 10^{-3}$ mg/mL.

Micelles of PEG-PEA(SS)-PEG block copolymer were prepared by dialysis method. DLS measurements show an average micelle size of 158 nm with a narrow size distribution (PDI=0.07) (FIG. 3). The critical micelle concentration (CMC), determined using pyrene as a probe, was estimated to be approximately 9.9 mg/L (FIG. 4).

Example 4

Reduction-Triggered Destabilization of PEG-PEA(SS)-PEG Micelles

Figure 5:
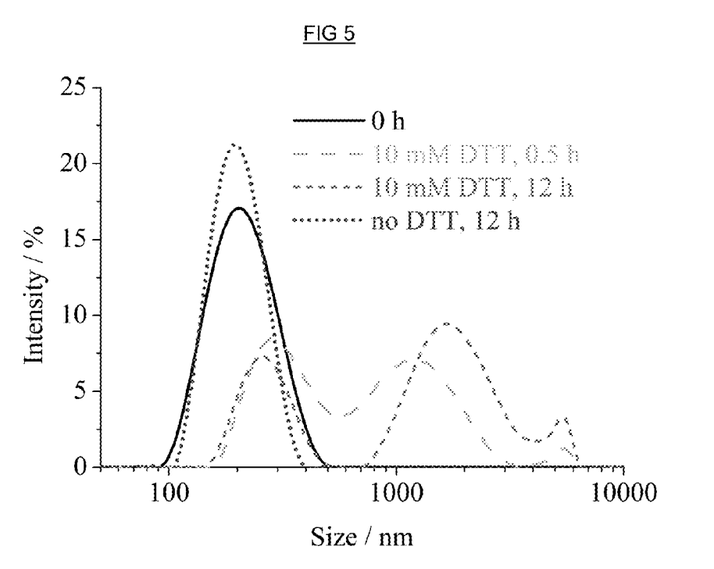
FIG. 5: The size change of PEG-PEA(SS)-PEG micelles in response to 10 mM DTT in PB buffer (10 mM, pH 7.4) determined by DLS
Figure 6:
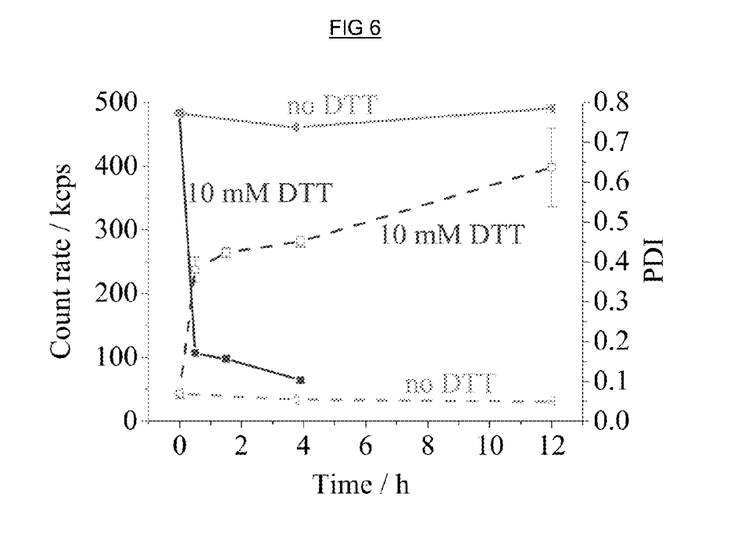
FIG. 6: Count rate/PDI change of PEG-PEA(SS)-PEG micelles in response to 10 mM DTT in PB buffer (10 mM, pH 7.4) determined by DLS.

The size change of micelles in response to 10 mM DTT in PB buffer (10 mM, pH 7.4) was followed by DLS measurement. Briefly, to 1.5 mL solution of PEG-PEA(SS)-PEG micelles in PB (10 mM, pH 7.4) previously degassed with nitrogen for 20 min, was added 10 mM DTT. The solution was placed in a shaking bed at 37° C. with a rotation speed of 200 rpm. At different time intervals, the size was determined using DLS. The size change of PEG-PEA(SS)-PEG micelles in response to 10 mM DTT in PB (10 mM, pH 7.4) was followed by DLS measurement. Notably, fast aggregation was observed for the micelles following addition of 10 mM DTT, in which micelle size increased from 160 nm to 325 nm (44%) and 1230 nm (54%) in 0.5 h, reaching over 1900 nm (62%) after 12 h (FIG. 5). Concomitantly, PDI increased from 0.07 to 0.64 after 12 h while the count rate decreased from 483 kcps to 64 kcps in 4 h (FIG. 6). Aggregates were formed due to most probably reductive cleavage of the repeated disulfide bonds, which results in water insoluble small molecules. In contrast, little change in micelle size, PDI and count rate is discerned after 12 h in the absence of DTT under otherwise the same conditions.

Example 5

Loading and Reduction-Triggered Release of DOX from PEG-PEA(SS)-PEG Micelles.

DOX was loaded into micelles by dropwise addition of 0.8 mL PB (10 mM, pH 7.4) to a mixture of 0.2 mL PEG-PEA(SS)-PEG copolymer solution in DMF (2 mg/mL) and DOX solution in DMSO (5 mg/mL) at varying DOX/polymer weight ratios (5-30 wt %) under stirring at r.t., followed by dialysis against PB (10 mM, pH 7.4) for 24 h at r.t. (MWCO 3500). The dialysis medium was changed five times. The whole procedure was performed in the dark. The amount of DOX was determined using fluorescence (FLS920) measurement (excitation at 480 nm and emission at 555 nm). For determination of drug loading content, lyophilized DOX loaded micelles were dissolved in DMSO and analyzed with fluorescence spectroscopy, wherein calibration curve was obtained with DOX/DMSO solutions with different DOX concentrations.

Drug loading content (DLC) and drug loading efficiency (DLE) are calculated according to the following formula:

DLC (wt. %)=[weight of loaded drug/(weight of polymer+drug)]×100%

DLE (%)=(weight of loaded drug/weight of drug in feed)×100%

The release profiles of DOX from PEG-PEA(SS)-PEG micelles were studied using a dialysis tube (MWCO 12000) at 37° C. in three different media, i.e. PB (10 mM, pH 7.4) only, PB (10 mM, pH 7.4) with 2 mM DTT or 5 mM DTT. In order to acquire sink conditions, drug release studies were performed at low drug loading contents (ca. 1.0 wt. %) and with 0.6 mL of micelle solution dialysis against 20 mL of the same medium. At desired time intervals, 6 mL release media is taken out and replenished with an equal volume of fresh media. The amount of DOX released was determined by using fluorescence (FLS920) measurement (excitation at 480 nm). The release experiments were conducted in triplicate. The results presented are the average data with standard deviations.

DOX is loaded into micelles by dialysis of a polymer/DOX solution in DMF against PB buffer. The theoretical drug loading content is set at 5, 10, 20 and 30 wt. %. The results show that PEG-PEA(SS)-PEG micelles encapsulated DOX efficiently, affording a drug loading efficiency between ca. 52% and 68% (Table 1).

TABLE 1

DOX loading content and loading efficiency with PEG-PEA(SS)-PEG micelles.

| Entry | Theoretical drug loading content (wt. %) | Micelle size$^a$ (nm) | PDI$^a$ | DOX loading content$^b$ (wt. %) | DOX loading efficiency (%) |
|---|---|---|---|---|---|
| 1 | 0 | 157.8 | 0.07 | — | — |
| 2 | 5 | 139.2 | 0.09 | 3.30 | 68.10 |
| 3 | 10 | 125.9 | 0.07 | 5.55 | 58.79 |
| 4 | 20 | 118.2 | 0.10 | 9.85 | 54.66 |
| 5 | 30 | 129.8 | 0.07 | 13.53 | 52.16 |

$^a$The average size and polydispersity index (PDI) of micelles determined by DLS measurements.
$^b$Determined by fluorescence measurement.

Figure 7:
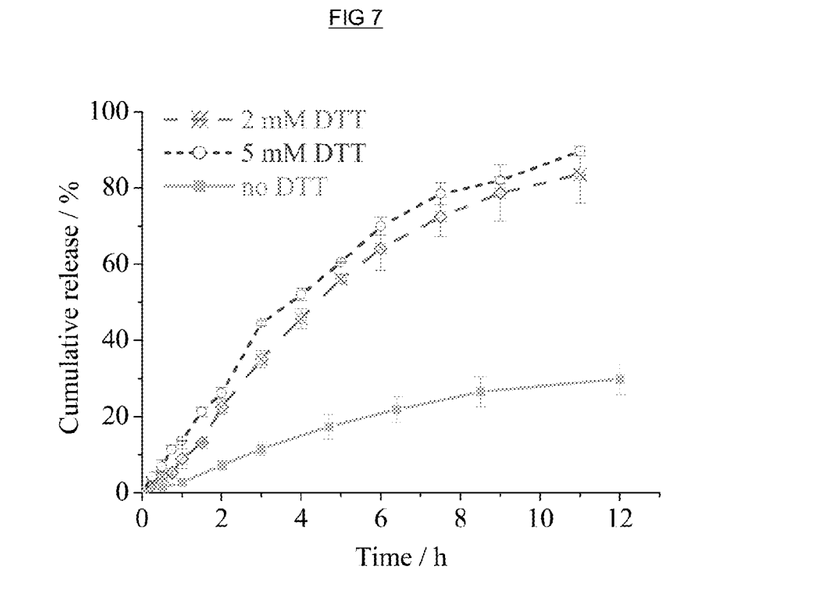
FIG. 7: Reduction-triggered release of DOX from PEG-PEA(SS)-PEG micelles in PB (10 mM, 7.4) at 37° C. in the presence or absence of DTT.

The release of DOX form PEG-PEA(SS)-PEG micelles is studied using a dialysis tube (MWCO 12000) in pH 7.4 PB buffer at 37° C. in the presence or absence of DTT. Remarkably, the results show that PEG-PEA(SS)-PEG micelles released DOX rapidly in the presence of 2 or 5 mM DTT, a reductive environment analogous to that of the intracellular compartments such as cytosol and the cell nucleus and 83% or 90% DOX is released after 11 h, respectively. In contrast, minimal drug release (<30%) is observed within 12 h in the absence of DTT (FIG. 7)

It is observed that fast drug release from PEG-PEA(SS)-PEG micelles is triggered by reduction. This is in line with the previous observation that PEG-PEA(SS)-PEG micelles are destabilized and form aggregates quickly in response to 10 mM DTT. It should be further noted that no burst release is observed and DOX is released from PEG-PEA(SS)-PEG micelles in a zero order manner up to 70% release. This constant release rate indicates that release of DOX is controlled most likely by a combination of diffusion and degradation.

Example 6

Cellular Uptake and Intracellular Release of DOX

HeLa cells are plated on microscope slides in a 24-well plate ($5\times10^4$ cells/well) under 5% $CO_2$ atmosphere at 37° C. using Dulbecco's modified Eagle's medium (DMEM) supplemented with 10% fetal bovine serum, 1% L-glutamine, antibiotics penicillin (100 IU/mL), and streptomycin (100 µg/mL). After 24 h, 50 µL of PB (10 mM, pH 7.4) solution of DOX-loaded PEG-PEA(SS)-PEG micelles or free DOX (DOX dosage: 12.5 µg/mL) is added. After incubation at 37° C. and a humidified 5% $CO_2$-containing atmosphere for 0.5, 2 or 4 h, the culture media are removed and the cells on microscope plates are washed three times with PBS. The cells are then fixed with 4% formaldehyde for 15 min and washed with PBS 3 times. The cell nuclei are stained with 4',6-diamidino-2-phenylindole (DAPI, blue) for 15 min and washed with PBS 3 times.

The cellular uptake and intracellular release behaviors of DOX-loaded PEG-PEA(SS)-PEG micelles are followed with CLSM using HeLa cells. Remarkably, strong DOX fluorescence in the cells is clearly observed in the cytosol as well as the cell nucleus after just 0.5 h incubation with DOX-loaded PEG-PEA(SS)-PEG micelles, indicating fast internalization of micelles and rapid release of DOX inside cells. This is in accordance with the expectation that disulfide bonds are cleaved in the intracellular compartments such as the cytosol and the cell nucleus due to presence of comparatively high concentrations of reducing glutathione tripeptides (2~10 mM). The fluorescence intensity of DOX inside cells and the amount of DOX transported into the cell nucleus increased further when increasing the incubation time to 2 and 4 h. In comparison, free DOX is mainly accumulated in cell nucleus.

Example 7

Cell Viability Assay

HeLa and MCF-7 cells are plated in a 96-well plate ($1\times10^4$ cells/well) using DMEM medium supplemented with 10% fetal bovine serum, 1% L-glutamine, antibiotics penicillin (100 IU/mL), and streptomycin (100 µg/mL) and incubation for 24 h. The cells are incubated with blank PEG-PEA(SS)-PEG micelles, DOX loaded PEG-PEA(SS)-PEG micelles, or free DOX (DOX dosage: 12.5 or 25 µg/mL) for 24 and 48 h at 37° C. in a humidified 5% $CO_2$-containing atmosphere. Then 3-(4,5-dimethylthiazol-2-yl)-2,5-diphenyl tetrazoliumbromide (MTT) solution in PBS (10 µL, 5 mg/mL) are added and incubated for another 4 h. The medium is aspirated, the MTT-formazan generated by live cells is dissolved in 150 µL of DMSO, and the absorbance at a wavelength of 490 nm of each well is measured using a microplate reader. The relative cell viability (%) is determined by comparing the absorbance at 490 nm with control wells containing only cell culture medium. Data are presented as average±SD (n=4).

Figure 8:
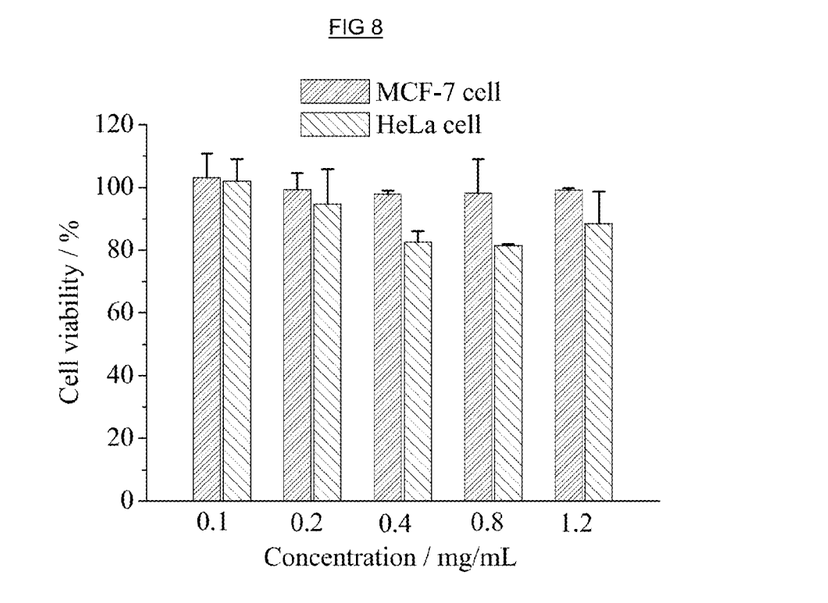
FIG. 8: Cytotoxicity of PEG-PEA(SS)-PEG micelles determined via MTT assays in HeLa and MCF-7 cells. The cells are incubated with micelles for 24 h. Data are presented as the average±standard deviation (n=4).

The cytotoxicity of blank PEG-PEA(SS)-PEG micelles is evaluated in HeLa and MCF-7 cells using MTT assays. The results revealed that these PEG-PEA(SS)-PEG micelles are practically nontoxic to HeLa (cell viability: 81.5-102.0%) and MCF-7 cells (cell viability: 97.8-103.2%) at varying concentrations from 0.1 to 1.2 mg/mL (FIG. 8), indicating that PEG-PEA(SS)-PEG micelles possess excellent biocompatibility.

Figure 9:
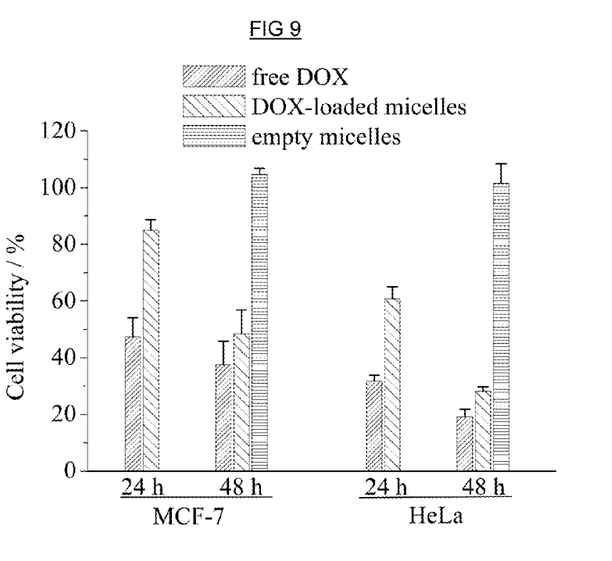
FIG. 9: The anti-tumor activity of DOX-loaded PEG-PEA (SS)-PEG micelles versus free DOX in HeLa and MCF-7 cells. DOX dosage was 12.5 µg/mL. The cells were incubated with DOX-loaded micelles or free DOX for 24 h or 48 h.
Figure 10:
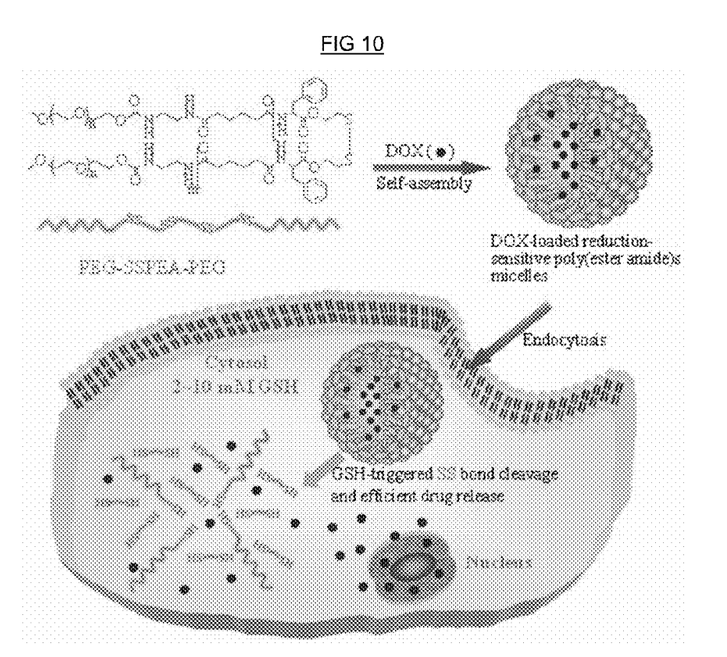
FIG. 10: Intracellular drug release and anti-tumor activity of drug-loaded PEG-PEA-SS-PEG micelles.

The anti-tumor activity of DOX-loaded PEG-PEA(SS)-PEG nanoparticles is also investigated via MTT assays. HeLa and MCF-7 cells are treated for 24 or 48 h with free DOX or DOX-loaded micelles (DOX dosage: 12.5 µg/mL). It should be noted that, after 24 h incubation, DOX-loaded PEG-PEA(SS)-PEG micelles exhibited lower toxicity to both the HeLa and MCF-7 cells than free DOX (cell viabilities of 31.8% and 47.4%, respectively) (FIG. 9). However, comparable cell viabilities are observed following 48 h incubation with DOX-loaded PEG-PEA(SS)-PEG micelles and free DOX to HeLa cells (cell viabilities 28.1% versus 19.1%) as well as MCF-7 cells (cell viabilities 48.4% versus 37.5%).

The invention claimed is:

1. An amphiphilic block copolymer comprising hydrophilic bocks and hydrophobic blocks, wherein the hydrophobic blocks comprise a biodegradable polyesteramide comprising disulphide linkages in the backbone of the biodegradable polyesteramide.

2. The amphiphilic block copolymer according to claim 1, wherein the biodegradable polyesteramide comprise residues of alpha-amino acids, diols, aliphatic dicarboxylic acids, and optionally diamines, wherein at least one of the diols, aliphatic dicarboxylic acids, or diamines comprises a disulphide linkage.

3. The amphiphilic block copolymer according to claim 1, wherein the biodegradable polyesteramide comprises a residue of at least one of the following structural formulas I, II or III, or a combination thereof:

Formula I

Formula II

-continued

Formula III wherein m is from 5 to 300;

Y is a ($C_2$-$C_{20}$) aliphatic hydrocarbons or a ($C_2$-$C_{20}$) cycloaliphatic hydrocarbons;

X is independently an aliphatic hydrocarbon, a cycloaliphatic hydrocarbon, or an aromatic hydrocarbon; and R is independently a side chain residue of arginine, histidine lysine, aspartic acid, glutamic acid, serine, threonine, asparginine, glutamines, cysteine, seleno cysteine, glycine, proline, alanine, valine, isoleucine, leucine, methionine, tyrosine, tryptophan, or phenylalanine.

4. The amphiphilic block copolymer according to claim 3, wherein X is an aliphatic $C_2$-$C_8$ hydrocarbon.

5. The amphiphilic block copolymer according to claim 3, wherein Y is ($C_2$-$C_{20}$)alkylene, ($C_2$-$C_{20}$) alkenylene, bicyclic-fragments of 1,4:3,6-dianhydrohexitols of structural Formula (IV), or combinations thereof Formula IV 6. The amphiphilic block copolymer according to claim 3, wherein the hydrophobic block comprises a residue of structural Formula I, wherein X is a ($C_2$-$C_{20}$) alkylene or ($C_2$-$C_{20}$) alkenylene and R is a side chain residue of arginine or phenylalanine.

7. The amphiphilic block copolymer according to claim 5, wherein the hydrophobic block comprises a residue of structural Formula I, wherein X is a ($C_2$-$C_{20}$) alkylene or ($C_2$-$C_{20}$) alkenylene and R is a side chain residue of arginine or phenylalanine.

8. The amphiphilic block copolymer according to claim 3, wherein the hydrophilic blocks comprise poly(ethylene oxide), polyvinylpyrrolidone, or polyoxazoline.

9. The amphiphilic block copolymer according to claim 7, wherein the hydrophilic blocks comprise poly(ethylene oxide).

10. The amphiphilic block copolymer according claim 1, wherein the amphiphilic block copolymer is a triblock copolymer.

11. The amphiphilic block copolymer according to claim 3, wherein the amphiphilic block copolymer is a triblock copolymer, the hydrophilic block comprises poly(ethylene oxide), and the hydrophobic block comprises a residue of structural formula I wherein R is a side chain residue of arginine or phenylalanine.

12. The amphiphilic block copolymer according to claim 7, wherein the amphiphilic block copolymer is a triblock copolymer and the hydrophilic block comprises poly(ethylene oxide).

13. A drug delivery system comprising micelles comprising the amphiphilic block copolymer according to claim 1.

14. A drug delivery system comprising micelles comprising the amphiphilic block copolymer according to claim 3.

15. A drug delivery system comprising micelles comprising the amphiphilic block copolymer according to claim 12.

16. The drug delivery system according to claim 13, wherein the micelles further comprise a hydrophobic drug.

17. The drug delivery system according to claim 14, wherein the micelles further comprise an anticancer drug.

18. The drug delivery system according to claim 16, wherein the hydrophobic drug is an anticancer drug.

19. The drug delivery system according to claim 17, wherein the average particle size of the micelles is from 10 to 400 nm.

20. The drug delivery system according to claim 18, wherein the average particle size of the micelles is from 10 to 400 nm.

* * * * *